US010993935B2

(12) United States Patent
Yu et al.

(10) Patent No.: US 10,993,935 B2
(45) Date of Patent: May 4, 2021

(54) COMPOSITIONS AND METHODS FOR TREATMENT OF LUNG INFECTIONS

(71) Applicant: MARSHALL UNIVERSITY RESEARCH CORPORATION, Huntington, WV (US)

(72) Inventors: Hongwei Yu, Huntington, WV (US); Thomas Ryan Withers, Huntington, WV (US); Brandon Kirby, Bluefield, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 16/429,153

(22) Filed: Jun. 3, 2019

(65) Prior Publication Data

US 2019/0365722 A1    Dec. 5, 2019

Related U.S. Application Data

(60) Provisional application No. 62/814,010, filed on Mar. 5, 2019, provisional application No. 62/679,292, filed on Jun. 1, 2018.

(51) Int. Cl.
| | | |
|---|---|---|
| *A61K 31/437* | (2006.01) | |
| *A61K 31/7036* | (2006.01) | |
| *A61K 9/00* | (2006.01) | |

(52) U.S. Cl.
CPC .......... *A61K 31/437* (2013.01); *A61K 9/0078* (2013.01); *A61K 31/7036* (2013.01)

(58) Field of Classification Search
CPC .................................................. A61K 31/437
USPC ......................................................... 514/300
See application file for complete search history.

(56) References Cited

U.S. PATENT DOCUMENTS

| | | | |
|---|---|---|---|
| 8,003,118 | B2 | 8/2011 | Kodsi |
| 8,642,573 | B2 | 2/2014 | Forbes et al. |
| 2006/0210483 | A1 | 9/2006 | Kodsi |

OTHER PUBLICATIONS

Chmiel et al., Ann. Am. Thorac. Soc., (2014), vol. 11(7), pp. 1120-1129.*
Ricci et al., J. Chemo. (2016), vol. 29(2), pp. 67-73.*
Biofilm—Wikipedia, visited Jan. 29, 2020.*
Gorbach et al., Probl Tuberk (1991) vol. 3, pp. 34-36. Abstarct.*
Laxer et al. Chemotheraoy (1975), 21(2), pp. 1-2.*
MedChem Express, MCE Rifaximin: CAS 80621-81-4 (2013), pp. 1-3.*
Aloush V, Navon-Venezia S, Seigman-Igra Y, Cabili S, Carmeli Y. 2006. Multidrug-resistant Pseudomonas aeruginosa: risk factors and clinical impact. Antimicrob Agents Chemother 50:43-8.
Boucher JC, Yu H, Mudd MH, Deretic V. 1997. Mucoid Pseudomonas aeruginosa in cystic fibrosis: characterization of muc mutations in clinical isolates and analysis of clearance in a mouse model of respiratory infection. Infect Immun 65:3838-46.
Nasirmoghadas P, Yadegari S, Moghim S, Esfahani BN, Fazeli H, Poursina F, Hosseininassab SA, Safaei HG. 2018. Evaluation of Biofilm Formation and Frequency of Multidrug-resistant and Extended Drug-resistant Strain in Pseudomonas aeruginosa Isolated from Burn Patients in Isfahan. Adv Biomed Res 7:61.
Head NE, Yu H. 2004. Cross-sectional analysis of clinical and environmental isolates of Pseudomonas aeruginosa: biofilm formation, virulence, and genome diversity. Infect Immun 72:133-44.
Ciofu O, Tolker-Nielsen T, Jensen PO, Wang H, Hoiby N. 2015. Antimicrobial resistance, respiratory tract infections and role of biofilms in lung infections in cystic fibrosis patients. Adv Drug Deliv Rev 85:7-23.
Yu H, Hanes M, Chrisp CE, Boucher JC, Deretic V. 1998. Microbial pathogenesis in cystic fibrosis: pulmonary clearance of mucoid Pseudomonas aeruginosa and inflammation in a mouse model of repeated respiratory challenge. Infect Immun 66:280-8.
Anderson GG, Moreau-Marquis S, Stanton BA, O'Toole GA. 2008. In vitro analysis of tobramycin-treated Pseudomonas aeruginosa biofilms on cystic fibrosis-derived airway epithelial cells. Infect Immun 76:1423-33.
Nichols WW, Dorrington SM, Slack MP, Walmsley HL. 1988. Inhibition of tobramycin diffusion by binding to alginate. Antimicrob Agents Chemother 32:518-23.
Hoffman LR, D'Argenio DA, Maccoss MJ, Zhang Z, Jones RA, Miller SI. 2005. Aminoglycoside antibiotics induce bacterial biofilm formation. Nature 436:1171-5.
Macleod DL, Nelson LE, Shawar RM, Lin BB, Lockwood LG, Dirk JE, Miller GH, Burns JL, Garber RL. 2000. Aminoglycoside-resistance mechanisms for cystic fibrosis Pseudomonas aeruginosa isolates are unchanged by long-term, intermittent, inhaled tobramycin treatment. J Infect Dis 181:1180-4.
Iorio N, Malik Z, Schey R. 2015. Profile of rifaximin and its potential in the treatment of irritable bowel syndrome. Clin Exp Gastroenterol 8:159-67.
Mullen KD, Sanyal AJ, Bass NM, Poordad FF, Sheikh MY, Frederick RT, Bortey E, Forbes WP. 2014. Rifaximin is safe and well tolerated for long-term maintenance of remission from overt hepatic encephalopathy. Clin Gastroenterol Hepatol 12:1390-7 e2.
Brown EL, Xue Q, Jiang ZD, Xu Y, Dupont HL. 2010. Pretreatment of epithelial cells with rifaximin alters bacterial attachment and internalization profiles. Antimicrob Agents Chemother 54:388-96.

(Continued)

*Primary Examiner* — Taofiq A Solola
(74) *Attorney, Agent, or Firm* — Stites & Harbison, PLLC; Terry L. Wright

(57) ABSTRACT

Methods of treating a bacterial lung infection are provided and comprise administering an effective amount of rifaximin to a subject in need thereof. The rifaximin can be delivered by inhalation therapy, such as by delivering the rifaximin in aerosol form. The rifaximin is administered alone or in combination with tobramycin, including in multiple doses. Methods of reducing biofilm formation are also provided and comprise contacting a bacteria with an effective amount of rifaximin. Pharmaceutical composition are also included and comprise rifaximin and a pharmaceutically-acceptable vehicle suitable for administering the rifaximin in aerosol form.

15 Claims, 9 Drawing Sheets

(56) References Cited

OTHER PUBLICATIONS

Rothstein JD, Patel S, Regan MR, Haenggeli C, Huang YH, Bergles DE, Jin L, Dykes Hoberg M, Vidensky S, Chung DS, Toan SV, Bruijn LI, Su ZZ, Gupta P, Fisher PB. 2005. Beta-lactam antibiotics offer neuroprotection by increasing glutamate transporter expression. Nature 433:73-7.

Stavrovskaya IG, Narayanan MV, Zhang W, Krasnikov BF, Heemskerk J, Young SS, Blass JP, Brown AM, Beal MF, Friedlander RM, Kristal BS. 2004. Clinically approved heterocyclics act on a mitochondrial target and reduce stroke-induced pathology. J Exp Med 200:211-22.

Cao B, Christophersen L, Kolpen M, Jensen PO, Sneppen K, Hoiby N, Moser C, Sams T. 2016. Diffusion Retardation by Binding of Tobramycin in an Alginate Biofilm Model. PLoS One 11:e0153616.

Long TE, Keding LC, Lewis DD, Anstead MI, Withers TR, Yu HD. 2016. Anionic fluoroquinolones as antibacterials against biofilm-producing Pseudomonas aeruginosa. Bioorg Med Chem Lett 26:1305-9.

Withers TR, Heath DF, Yin Y, Yu HD. 2013. Truncation of type IV pilin induces mucoidy in Pseudomonas aeruginosa strain PAO579. Microbiologyopen 2:459-70.

Figurski DH, Helinski DR. 1979. Replication of an origin-containing derivative of plasmid RK2 dependent on a plasmid function provided in trans. Proc. Natl. Ac.ad. Sci. USA 76, 1648-1652, vol. 76.

AL Ahmar R, Kirby BD, Yu HD. 2018. Pyrimidine Biosynthesis Regulates Small Colony Variant and Mucoidy in Pseudomonas aeruginosa Through Sigma Factor Competition. J Bacteriol doi:10.1128/JB.00575-18.

Sheppard JG, Mcaleer JP, Saralkar P, Geldenhuys WJ, Long TE. 2018. Allicin-inspired pyridyl disulfides as antimicrobial agents for multidrug-resistant *Staphylococcus aureus*. Eur J Med Chem 143:1185-1195.

Wilson KR, Napper JM, Denvir J, Sollars VE, Yu HD. 2007. Defect in early lung defense against Pseudomonas aeruginosa in DBA/2 mice is associated with acute inflammatory lung injury and reduced bactericidal activity in naive macrophages. Microbiology 153:968-79.

Preston MJ, Seed PC, Toder DS, Iglewski BH, Ohman DE, Gustin JK, Goldberg JB, Pier GB. 1997. Contribution of proteases and LasR to the virulence of Pseudomonas aeruginosa during corneal infections. Infection and Immunity 65:3086-3090.

Kirby BD, Al Ahmar R, Withers TR, Valentine ME, Valentovic M, Long TE, Gaskins JR, Yu HD. 2019. Efficacy of Aerosolized Rifaximin versus Tobramycin for Treatment of Pseudomonas aeruginosa Pneumonia in Mice. Antimicrobial Agents and Chemotherapy 63:1-13.

Kirby, et al. "Comparison of Tobramycin vs. Rifaximin Aerosol Therapy Efficacy for Treatment of Acute Pseudomona aeruginosa Pneumonia in Mice." Poster Presentation, American Society of Microbiology Conference, Jun. 4, 2017.

Galvao J, Davis B, Tilley M, Normando E, Duchen MR, Cordeiro MF. 2014. Unexpected low-dose toxicity of the universal solvent DMSO. FASEB J 28:1317-30.

Sachetelli S, Beaulac C, Lagace J. 1998. Aminoglycoside detection using a universal ELISA binding procedure onto polystyrene microtiter plates in comparison with HPLC analysis and microbiological agar-diffusion assay. Biochim Biophys Acta 1379:35-41.

Rao RN, Vali RM, Rao AV. 2012. Determination of rifaximin in rat serum by ionic liquid based dispersive liquid-liquid microextraction combined with RP-HPLC. J Sep Sci 35:1945-52.

\* cited by examiner

COMPOSITIONS AND METHODS FOR TREATMENT OF LUNG INFECTIONS

RELATED APPLICATIONS

This application claims priority from U.S. Provisional Application Ser. No. 62/814,010, filed Mar. 5, 2019, and U.S. Provisional Application Ser. No. 62/679,292, filed Jun. 1, 2018, the entire disclosures of which are incorporated herein by this reference.

GOVERNMENT INTEREST

This invention was made with government support under grant numbers R44GM113545 and P20GM103434 awarded by the National Institutes of Health. The government has certain rights in the invention.

TECHNICAL FIELD

The presently-disclosed subject matter relates to compositions and methods for treatment of lung infections. In particular, certain embodiments of the presently-disclosed subject matter relate to compositions and methods for treatment of bacterial lung infections that make use of an aerosolized form of rifaximin.

BACKGROUND

*Pseudomonas aeruginosa* is a gram-negative rod shaped bacteria. *P. aeruginosa* is abundant in the environment, but can be an opportunistic pathogen for immunocompromised individuals, such as burn victims. *P. aeruginosa* is also responsible for hospital-acquired infections and ventilator-associated pneumonia. Virulence factors that make this bacteria toxic include multidrug resistance and biofilm formation. Biofilms are formed when colonies aggregate and form an extracellular matrix that provides an anchor point for new cells as well as protection from environmental dangers including antibiotics and immune responses.

The population with the highest risk for an infection by *P. aeruginosa* are cystic fibrosis patients. Cystic fibrosis is a genetic disease that causes malfunction in mucus cells in various organ systems. These patients experience an over-production of thick and viscous mucus in the lungs and airway. This mucus makes the host lung a perfect environment for the production of biofilms and the aggregation of *P. aeruginosa*. The growth of biofilms cause a chronic pneumonia that causes difficulty breathing and decreased lung function, as well as an increase in mortality in cystic fibrosis patients. In this regard, although the current definition of a biofilm defines a wide range of situations, alginate formation is commonly representative of biofilm formation. Alginate is a matrix made of guluronic and mannuronic acid formed by *P. aeruginosa*. The phenotype of alginate overproduction by *P. aeruginosa* is known as mucoid, and is a prevalent phenotype in cystic fibrosis isolated strains.

Current treatment for cystic fibrosis patients is inhaled tobramycin in multiple treatments on a daily basis. Tobramycin is an aminoglycoside antibiotic with a narrow spectrum against gram-negative bacteria, specifically *P. aeruginosa* species. However, recent studies have suggested that tobramycin is not an optimal treatment for cystic fibrosis patients. The first issue with the use of tobramycin is the inhibited penetration of tobramycin into biofilm producing species, which are found in most CF lungs. Researchers have found that tobramycin does not penetrate biofilms sufficiently by using columns with biofilm growth and measuring tobramycin concentrations at the top and bottom after administration of the drug. Another study achieved similar results using alginate beads and measuring concentration of tobramycin on the surface and inside of the bead after administration. Concentrations of tobramycin were severely diminished inside the alginate beads or through the biofilm columns in both studies.

Another issue with the use of tobramycin is the increasing resistance of *P. aeruginosa* and other pathogenic bacteria to aminoglycosides. A recent study using cystic fibrosis isolates from various locations throughout the United States had a high percentage of tobramycin resistance. This leads to a diminished effect by the drug and an increase in more severe and fatal infections. Lastly, recent studies have shown that use of aminoglycosides against biofilm forming species like *P. aeruginosa* species leads to aminoglycoside induced biofilm formation. This situation creates a negative feedback loop in which the use of tobramycin induces the production of biofilms, which leads to a decrease in efficacy due to resistance and decreased penetration.

Accordingly, an alternative treatment for lung infections, including *P. aeruginosa* infections in cystic fibrosis patients, would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes compositions and methods for treatment of bacterial lung infections that make use of rifaximin, including, in certain embodiments, an aerosolized form of rifaximin. In some embodiments, a method of treating a bacterial lung infection is provided that comprises administering to a subject in need thereof an effective amount of rifaximin. In some embodiments, the subject has a bacterial lung infection. In some embodiments, the subject has cystic fibrosis.

For administration of the rifaximin, in some embodiments, administering the rifaximin comprises administering the rifaximin by inhalation delivery. In some embodiments, the rifaximin is in aerosolized form. In some embodiments, administering the rifaximin further comprises co-administering an effective amount of tobramycin to the subject. In some embodiments, the rifaximin and/or the tobramycin are administered in multiple doses. In some embodiments, the tobramycin is in aerosolized form.

In some embodiments of the therapeutic methods described herein, the bacterial lung infection comprises an antibiotic-resistant bacterial lung infection. In some embodiments, the bacterial lung infection comprises an infection by a bacteria selected from the group consisting of *Pseudomonas aeruginosa, Staphylococcus aureus, Burkholderia cepa-*

*cia*, and *Stenotrophomonas maltophilia*. In some embodiments, the bacterial lung infection is acute pneumonia.

In some embodiments of the therapeutic methods, administering the rifaximin reduces an amount of biofilm produced from or associated with the bacterial lung infection. In some embodiments, the rifaximin is administered in an amount effective to reduce an amount of alginate production.

Further provided, in some embodiments of the presently-disclosed subject matter are methods of reducing biofilm formation or aggregation. In some embodiments, a method of reducing biofilm formation or aggregation is provided that comprises contacting a bacteria with an effective amount of rifaximin and an effective amount of tobramycin.

Still further provided, in some embodiments, are pharmaceutical compositions comprising rifaximin and a pharmaceutically-acceptable vehicle suitable for administering the rifaximin in aerosol form. In some embodiments, such pharmaceutical compositions further comprise tobramycin.

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1A:
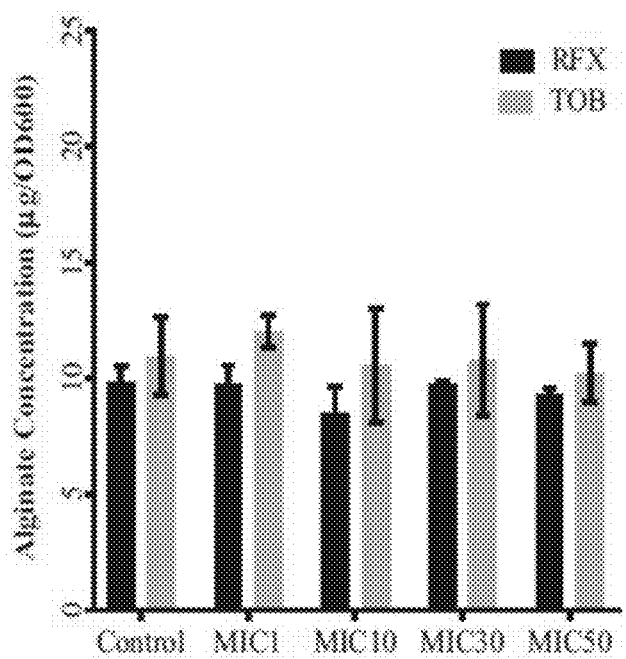
FIGS. 1A-1D includes graphs showing rifaxamin (RFX) is more potent than tobramycin (TOB) for inhibition of alginate production of laboratory and cystic fibrosis (CF) sputum isolates of *P. aeruginosa*, including graphs showing alginate production for nonmucoid reference strain PAO1 (FIG. 1A), PAO581 (PAO1mucA25) (FIG. 1B), and stable mucoid clinical isolates CF001 (FIG. 1C) and CF010 (FIG. 1D) when grown on PIA at 37° C. for 24 h with increasing concentrations of RFX or TOB according to the predetermined MIC. Data shown represent means of 5 replicates per group ±standard error (SE). Two-way ANOVA analysis was used with statistical significance set as a P value of <0.01 (**, P<0.0001; , P<0.001; *, P<0.01).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes compositions and methods for treatment of lung infections. In particular, certain embodiments of the presently-disclosed subject matter include compositions and methods for treatment of bacterial lung infections that make use of an aerosolized form of rifaximin (RFX). Rifaximin has been approved by the Food and Drug Administration (FDA) to treat traveler's diarrhea and hepatic encephalopathy as a semi-synthetic non-systematic antibiotic. It is also appreciated that the target of rifaximin is bacterial RNA polymerase and that, at low concentrations, rifaximin can inhibit biofilm formation via inhibiting an alginate regulator. It has now been further determined that rifaximin can be suitably formulated in a aerosolized form and administered to a subject for the treatment of lung infections, including bacterial lung infections caused by antibiotic-resistant bacterial strains. Moreover, it has been surprisingly found that the inhalation administration of rifaximin can be combined with other inhaled antibiotics in a synergistic manner.

Rifaximin

In some embodiments of the present invention, a method of treating a bacterial lung infection is thus provided that comprises administering to a subject in need thereof an effective amount of rifaximin. In some embodiments, administering the rifaximin comprises administering the rifaximin by inhalation delivery. In some embodiments, the rifaximin is in aerosolized form.

The term "bacterial lung infection," as used herein, is used to refer to any infection caused or exacerbated by the proliferation of bacteria within the lungs of a subject. Such infections may be present in the larger airways of the lungs (e.g., as with bronchitis) or in the smaller air sacs of the lungs (e.g., as with pneumonia), but are generally characterized by a build-up of fluid in the lungs and increasing swelling within the lungs. Additional symptoms commonly associated with such bacterial lung infections include, but are not limited to, fast or difficulty breathing, coughing with brown or green-colored phlegm, fever, a general feeling of unwellness, cyanosis, stomach pain, chest pain, headaches, general aches and pains, loss of appetite, and the like.

As used herein, the terms "treatment" or "treating" relates to any treatment of a bacterial lung infection, including but not limited to prophylactic treatment and therapeutic treatment. As such, the terms "treatment" or "treating" include, but are not limited to reducing the severity of a bacterial lung infection; inhibiting the progression of a bacterial lung infection; arresting or reducing the further development of a bacterial lung infection; ameliorating or relieving symptoms associated with a bacterial lung infection; and causing a regression of a bacterial lung infection or one or more of the symptoms associated with a bacterial lung infection. In some embodiments of the therapeutic methods, the subject has a bacterial lung infection. In some embodiments, the subject has cystic fibrosis.

For administration of a therapeutic composition as disclosed herein (e.g., a pharmaceutical composition comprising rifaximin), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, and as described in further detail below, the therapeutic compositions are administered by inhalation to thereby treat a bacterial lung infection.

Regardless of the route of administration, the therapeutic agents used in accordance with the presently-disclosed subject matter are typically administered in an amount effective to achieve the desired response. As such, the term "effective amount" is used herein to refer to an amount of the therapeutic composition sufficient to produce a measurable biological response (e.g., a decrease in bacterial infection). Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

With respect to bacterial lung infections capable of being treated in accordance with the presently-disclosed subject matter, in some embodiments, the bacterial lung infection comprises an antibiotic-resistant bacterial lung infection or, in other words, a lung infection that is the result of bacteria that have become resistant to antibiotics typically used to treat an infection or to typical dosages of those antibiotics, such as what may occur due to changes in the bacteria themselves (e.g., genetic modification). In some embodiments, the bacterial lung infection comprises an infection by a bacteria selected from the group consisting of *Pseudomonas aeruginosa, Staphylococcus aureus* (e.g., methicillin resistant *S. aureus*), *Burkholderia cepacia*, and *Stenotrophomonas maltophilia*. In some embodiments, the bacterial lung infection is acute pneumonia. In some embodiments, administering the rifaximin reduces an amount of biofilm produced from the bacterial lung infection and/or reduces an amount of alginate production to thereby treat the bacterial infection.

In some embodiments, the rifaximin administered to treat a bacterial lung infection in a subject can be administered alone or with no other antibiotics to treat the bacterial infection in the subject. In other embodiments, however, the rifaximin can be administered in conjunction with other therapeutic agents. In some embodiments, administering of the rifaximin with other therapeutic agents provides a synergistic effect where the observed therapeutic effect is greater than that observed when the therapeutic agents are administered alone and/or is greater than the therapeutic effects that would be observed when the individual therapeutic effects of those antibodies are simply added together. For instance, in certain embodiments, the rifaximin is administered in conjunction with an effective amount of tobramycin to the subject as doing so leads to an enhanced treatment of the bacterial lung infection in the subject. In some embodiments, tobramycin is also administered via inhalation or in aerosolized form to treat the infection. In some embodiments, and as described in further detail below, the rifaximin and/or tobramycin is administered at a concentration of about 60 mg/mL nebulized in 5 ml of a suitable solvent to thereby treat the bacterial lung infection.

With further respect to the co-administration of rifaximin and tobramycin, in some embodiments of the presently-disclosed subject matter, methods of reducing biofilm formation are thus further provided that comprise contacting a bacteria with an effective amount of rifaximin and an effective amount of tobramycin.

Still further provided, in some embodiments of the presently-disclosed subject matter, are pharmaceutical compositions including rifaximin and a pharmaceutically-acceptable carrier suitable for administering the rifaximin, such as a pharmaceutically-acceptable carrier suitable carrier for administering the rifaximin in aerosolized form. The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of compound to biodegradable polymer and the nature of the particular biodegradable polymer employed, the rate of compound release can be controlled. Depot injectable formulations can also be prepared by entrapping the compound in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the compounds can be in powder form for constitution with a suitable vehicle before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

In some embodiments, a pharmaceutical composition is provided that comprises rifaximin and a pharmaceutically-acceptable vehicle or carrier that is suitable for administering the rifaximin in aerosol form. The term "aerosol" refers to a formulation that is deliverable in the form of a dispersion of a solid and/or liquid in a gas. These can be prepared from suspensions of the formulation in a liquid, using a device such as a nebulizer, or from dry powders using a dry powder inhaler for administration to a subject.

In some embodiments, such a pharmaceutical composition further comprises tobramycin. In some embodiments, the tobramycin, like the rifaximin, is also provided in a suitable vehicle or carrier for delivery in aerosol form. In some embodiments, given rifaximin's poor solubility in aqueous vehicles, the vehicle comprises dimethyl sulfoxide (DMSO) or another suitable organic solvent to create the aerosol formulation suitable for administration to a subject.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-7

Bacterial Strains, Plasmids, and Growth Conditions. All bacterial strains used in the study are listed in Table 1 below. *P. aeruginosa* strains were all grown on *Pseudomonas* Isolation Agar (PIA) plates (Difco, Detroit, Mich.) or *Pseudomonas* Isolation Broth (PIB) (Difco, Detroit, Mich.) at 37° C., prepared by adding 20 ml of glycerol/liter of media as recommended by the manufacturer. PIA was supplemented with 300 µg/ml of carbenicillin when necessary.

TABLE 1

Bacterial Strains and plasmids used in the study.

| Bacterial Strain or plasmid | Genotype, phenotype, or description |
| --- | --- |
| *P. aeruginosa* Strains | |
| PAO1 | Prototroph, NM |
| PAO581 | PAO1 mucA25, M |
| CF001 | CF Isolate, M |
| CF003 | CF Isolate, NM |
| CF010 | CF Isolate, M |
| Plasmids | |
| pRK2013 | Km$^r$, Tra Mob ColE1 |
| pLP170 | 8.3-kb, promoterless-lacZ, Ap$^r$, multiple cloning site |
| pLP170-P$_{algD}$ | Complete P$_{algD}$ promoter (989 bp upstream of ATG) fused with lacZ in pLP170 BamHI/HindII |
| pUC18-mini-Tn7T-lux | *Pseudomonas* suicide vector that carries luxCDABE operon for insertion into attTn7 sites |

Figure 7:
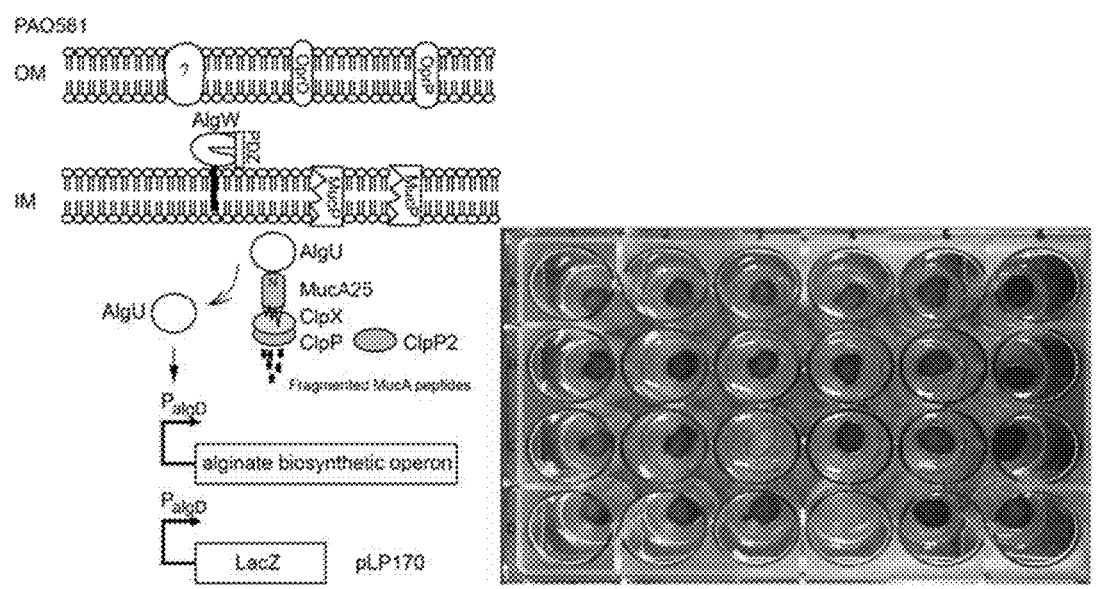
FIG. 7 includes a schematic diagram and an image depicting the use of an National Institutes of Health (NIH) drug library to scan for possible candidates to replace tobramycin (TOB), where rifaximin (RFX), a bacterial RNA inhibitor, was found to exhibit anti-biofilm activities.

Screen for Drug Candidates that Inhibits Growth and Alginate Production in *P. aeruginosa*. The drug collection library was assembled by the National Institutes of Health (NIH) through the Molecular Libraries Roadmap Initiative. It is called NIH clinical collections 1 and 2 (NCC plates 105 and 106) and contains 446 and 725 compounds, respectively (see, e.g., FIG. 7). The library was arrayed in 96-well plates as an approximately 10 mM solution in 100% DMSO. These small molecular weight compounds all have a history of safe use in human clinical trials and were curated and supplied by Evotec. Three concentrations of drugs (50, 10 and 2 µM) were used to screen for the inhibition of growth and alginate production in *P. aeruginosa*. A mucoid strain of *P. aeruginosa* PAO581 (PAO1mucA25), was introduced with plasmid pLP170 carrying the alginate biosynthetic promoter P$_{algD}$ fused with a promoterless lacZ operon. This strain was grown with about the same number of cells as adjusted by optical density for the screen on *Pseudomonas* isolation agar (PIA) supplemented with 5-bromo-4-chloro-3-indolyl-β-D-galactopyranoside (X-gal) to a final concentration of 20 µg/ml.

Minimum Inhibitory Concentration Testing. MIC testing was performed as previously described. Briefly, overnight culture of bacteria was diluted in 1:100 of a 0.5 McFarland standard as inoculum. The same number of cells was grown in LB broth containing serial, two-fold dilutions of rifaximin (RFX) or tobramycin (TOB). Growth was measured via optical density (OD) at 600 nm after 24 h incubation at 37° C. Concentrations of antibiotic required for inhibition of 50% and 90% of strains were determined.

Synergy Testing. Synergistic potential of RFX and TOB was performed by isobologram (checkerboard) analysis in 96-well plate format PIB. Briefly, PIB containing serial dilutions of each drug were plated in 64 wells of a 96-well plate with one drug vertically plated and the other horizontally plated. Bacterial cells of *P. aeruginosa* were grown 4 to 6 hours to an early log phase and then added to the wells of the plate. Growth in the wells was measured via OD at 600 nm after 24 h incubation at 37° C. The MIC and Fractional Inhibition Concentration (FIC) were calculated to determine synergism, antagonism or additivity between the tested strains of *P. aeruginosa*: PAO1, PAO581, PAO581 isogenic mutant, CF001, and CF010. The summative ΣFTC was calculated from the FICs and interpreted according to the standard index values: synergy ≤0.5; indifferent 0.5< to ≤4; antagonism >4.

Uronic Acid Carbazole Assay. Alginate production was measured via carbazole assay. Laboratory and clinical isolate strains were grown in PIB from a single colony isolation. The strains were then plated on 150 mm agar plates containing no antibiotic; RFX at concentrations of 10 µM (MIC$_{50}$), 6 µM (MIC$_{30}$), 2 µM (MIC$_{10}$), and 0.2 µM (MIC$_1$); or TOB at concentrations of 2 µM (MIC$_{50}$), 1.2 µM (MIC$_{30}$), 0.4 µM (MIC$_{10}$), and 0.04 µM (MIC$_1$) and incubated at 37° C. for 48 h. Sterile PBS (30 mL) was added to the plates and the cells plus their mucoid film were collected into 50 mL conical tubes. A 1 mL sample was taken to measure growth via OD at 600 nm. A 700 µL sample was then added to tubes containing 6 mL of a sulfuric acid-borate solution. A 200 µL aliquot of 0.1% carbazole was then added to the tubes and incubated for 30 m at 55° C. The alginate was then measured via OD at 530 nm and plotted against a standard curve made with D-mannuronic acid (Sigma-Aldrich). The reported values represent an average from three independent alginate collections with standard deviation.

Biofilm Reduction Assay. A biofilm reduction assay was used to determine the reduction of biofilms in *P. aeruginosa* strains by TOB and/or RFX. Briefly, biofilms were grown in a flat bottom 96-well microplate (Corning) using 200 µl LB of 1.0-1.5×10$^5$ inoculum of lab and clinical strains of non-mucoid and mucoid *P. aeruginosa*. After 24-30 h incubation at 37° C., the media was removed, and plates were washed with PBS. New media containing 1-5×MIC90 of TOB and/or RFX was added to the plate in a checkerboard pattern to determine synergy of biofilm reduction. After 24 h incubation at 37° C., the media was removed and 200 µl of 0.1% aqueous crystal violet was added and left at room temperature 0.5 h. The solution was then removed, plates were washed with PBS, and 200 µl of 30% acetic acid was added. The plates were then read via OD at 595 nm using SpectraMax i3x plate reader to compare biofilm dispersion between TOB and/or RFX.

Viable Cell Assay. Viable cell counts were done to determine the reduction of viable cells in preformed biofilms treated with TOB and/or RFX. Briefly, following biofilm reduction protocol, biofilms were grown in a flat bottom 96-well microplate (Corning) using 200 µl LB of 1.0-1.5× 10$^5$ inoculum of lab and clinical strains of non-mucoid and mucoid *P. aeruginosa* for 24 h at 37° C. After incubation, the media was removed, and plate was washed with PBS twice. New LB media containing 1-5×MIC$_{90}$ of TOB and/or RFX was added to the plate in a checkerboard pattern. After 24 h growth at 37° C., the media was removed and replaced with methylthiazoltetrazolium (MTT; Sigma). After 1 h incubation, DMSO was added and plates were read via OD at 570 nm using SpectraMax i3x plate reader to determine viable cell differences between TOB and/or RFX.

Mice. Protocols for murine lung infections and in vivo drug efficacy testing were approved by Marshall University Institutional Animal Care and Use Committee (IACUC).

Animals used in this study were obtained from Charles River Laboratories (Wilmington, Mass.). C57BL/6 mice were for the drug nebulization studies and DBA/2 mice were used for the murine *P. aeruginosa* pneumonia model. Mice were housed in the Marshall University Animal Facility under veterinary supervision. The age of mice tested were between 8 and 12 weeks. The weight of each mouse was taken prior to testing.

Drug Nebulization. C57BL/6 mice (n=8) were first exposed to 5 mL DMSO for 10 minutes to determine any adverse effects that may occur from using DMSO. Mice (n=16) were then exposed to TOB in 0.225% saline or RFX in DMSO via nebulization until the 5 mL drug mixture was depleted—typically 10-15 minutes. Nebulization was conducted using the pressure-based nebulizer and chamber purchased from Kent Scientific (Torrington, Conn.). TOB was nebulized at concentrations of 100 mg (n=4) or 400 mg (n=4) in 5 mL of 0.225% saline. RFX was nebulized at concentrations of 100 mg (n=4) or 400 mg (n=4) in 5 ml of 100% dimethyl sulfoxide. Mice were sacrificed immediately after nebulization via $CO_2$ chamber. Lungs were then collected and homogenized. TOB concentrations were measured using ELISA. RFX concentrations were measured via HPLC.

ELISA Analysis of TOB Tissue Concentration. TOB concentration in the lung tissue was measured via ELISA following a previously-established protocol. Briefly, a 96-well flat bottom micro-titer plate was coated with 0.1% alcian blue in 3% acetic acid and incubated for 30 min at 37° C. The plates were then washed twice with PBS and dried at RT. After drying, the plates were coated with TOB in carbonate buffer for generating the standard curve or with lung homogenate samples overnight at RT. The plates were then washed twice with PBS containing 0.05% Tween 20 (PBS-T). Skim milk in PBS-T was then added to the wells and incubated overnight at 37° C. The plates were washed with PBS-T and sheep IgG anti-TOB polyclonal antibody (Cat: PA175463; Thermo Scientific) was added and incubated 1 h at 37° C. The plates were then washed three times with PBS-T and HRP-conjugated rabbit anti-sheep IgG polyclonal antibody (Thermo Scientific) was added and incubated 1 h at 37° C. The plates were then washed three times with 0.05% PBS Tween 20 and TMB solution was added and incubated for 30 minutes at RT. Acid stop solution was added and absorbance was read on a SpectraMax spectrophotometer at 450 nm and 540 nm. Concentrations of TOB in lung samples were determined by reference to a standard curve generated with the known amount of HPLC grade TOB.

HPLC Analysis of RFX Tissue Concentration. HPLC analysis of RFX in the lung homogenates was performed to determine the amount of RFX retained in the mouse lungs using an adaptation of a previously-published method. Briefly, a Beckman HPLC system gold or a Waters Alliance HPLC system was used. The samples were centrifuged at 1000 g for 10 min and the supernatant collected. An aliquot of the supernatant was injected on a 5 micron Waters XTerra R18 Column (250 mm×4.6 mm). The mobile phase was a 45:55 mix of 0.1% acetic acid: acetonitrile with a flow rate of 1 ml/min. The detector was a Beckman photodiode array at 239 nm. The amount of RFX in lung samples was determined by reference to RFX standards analyzed by the same HPLC method.

Particle Size Analysis of Aerosol Drugs. Droplet size analysis of drugs used for aerosol therapy was conducted by Spray Analytics (Lincolnshire, Ill.). Samples of TOB in 0.225% saline and RFX in 100% DMSO at concentrations of 60 mg/mL for both were prepared and submitted along with nebulizer unit used for animal experiments. A Malvern Spraytec was used for analysis with the tested product sprayed horizontally at less than 5 cm from the detector beam. The samples were measured in triplicates for 20-30 seconds of stable operation of the nebulizer. Refractive index and absorption values used were that of DMSO for RFX and water for TOB.

Murine Pneumonia Model Treatment. TOB or RFX were used to treat *P. aeruginosa* respiratory infection in a DBA/2 mouse model established previously. Lung infection was induced by a single exposure to a total of 84 male DBA/2 mice of 8 week old (Charles River Laboratories) to *P. aeruginosa* PAO1 aerosols, which was prepared as previously reported. Immediately after infection, the mice were separated into seven groups (n=12 per group): 1) control with no treatment, 2) treatment with 300 mg TOB immediately after infection, 3) treatment with 300 mg RFX immediately after infection, 4) treatment with 300 mg TOB 6 h after infection, 5) treatment with 300 mg RFX 6 h after infection, 6) treatment with 300 mg TOB 12 h after infection, or 7) treatment with 300 mg RFX 12 h after infection. Each experimental group was treated with TOB or RFX with a control group treated with PBS following the nebulization protocol as described above. The mice were monitored for survival at 12 hour intervals for 72 hours and then at 24 hour intervals for 6 weeks.

Multiple doses of TOB with or without RFX were used to treat a *P. aeruginosa* respiratory infection in a DBA/2 mouse model established previously; however, the PAO1 strain used had a bioluminescent operon (luxCDABE). Female DBA/2 mice were infected at 0 hour and split into 3 experimental groups of 8: no treatment; treatment with 300 mg TOB at 6, 8, and 10 h post-infection; or treatment with 300 mg RFX at 6 h and 300 mg TOB at 8 and 10 h post-infection. Two mice from each group were sacrificed at 12, 18, and 24 h post-infection. Lungs from sacrificed mice were homogenized in 1% PPBS and tested for bacterial growth to determine CFU load per mouse. Bacteria grown were also imaged for evidence of bioluminescence. Two mice from each group were left to observe for survival.

Statistical Analysis. The one-way and two-way ANOVA, Kaplan-Meier plots and Mantel-Cox test were used to analyze the data, with statistical significance set at $p<0.01$. All statistical analysis was performed using GraphPad Prism version 7.02 for windows (GraphPad Software, La Jolla, Calif.)

Example 1—Screen of NIH Drug Library for Inhibition of Alginate Production by *P. Aeruginosa* Identified RFX Treatment with TOB cannot completely eradicate *P. aeruginosa* lung infections in CF as shown by various recent studies. To identify an alternative treatment strategy, a NIH drug library was screened, consisting of the 1,171 pharmacologically active compounds currently used in pharmaceuticals and/or clinical trials, for inhibition of alginate production, as well as growth inhibition activity against *P. aeruginosa*. Testing was performed in three concentrations of drugs (50, 10 and 2 µM). A reporter plasmid containing the promoters for the alginate algD biosynthetic operon attached to the lacZ operon was introduced into a stable mucoid laboratory strain of *P. aeruginosa* PAO581. Using this construct, a screen was conducted for growth and mucoidy inhibition, as well as alginate biosynthetic promoter activities. Fifteen of the drugs were identified as the inhibitors of mucoidy of *P. aeruginosa* (Table 2). Those drugs were further tested using a clinical mucoid isolate from a CF patient and determined that RFX was the most effective drug to inhibit the growth and mucoidy.

TABLE 2

NIH Drug Library Small Molecule Tested for Alginate Inhibition.

| | Mucoidy | | | Growth | | | Color | | |
|---|---|---|---|---|---|---|---|---|---|
| | 50 µM | 10 µM | 2 µM | 50 µM | 10 µM | 2 µM | 50 µM | 10 µM | 2 µM |
| Pazufloxacin | N/A | N/A | N/A | Inhibited | Inhibited | Inhibited | N/A | N/A | N/A |
| Moxifloxacin Hydrochloride | N/A | N/A | Reduced | Inhibited | Inhibited | Reduced | N/A | N/A | Light Blue |
| Rifabutin | N/A | N/A | High | Inhibited | Inhibited | Reduced | N/A | N/A | Light Blue |
| Pefloxacin Mesylate | N/A | N/A | Inhibited | Inhibited | Inhibited | Reduced | N/A | N/A | Light Blue |
| Levofloxacin | N/A | N/A | N/A | Inhibited | Inhibited | Inhibited | N/A | N/A | N/A |
| Carmofur | Inhibited | Inhibited | High | Reduced | Reduced | Yes | Clear | Clear | Light Blue |
| Tosufloxacin Tosilate | N/A | N/A | N/A | Inhibited | Inhibited | Inhibited | N/A | N/A | N/A |
| Clarithromycin | Inhibited | High | High | Yes | Reduced | Yes | Light Blue | Blue | Blue |
| Nisoldipine | Inhibited | High | No Test | Yes | Yes | No Test | Light Blue | Blue | No Test |
| Rufloxacin Monohydrate | Inhibited | High | No Test | Yes | Yes | No Test | Light Blue | Blue | No Test |
| Enrofloxacin | N/A | N/A | N/A | Inhibited | Inhibited | Inhibited | N/A | N/A | N/A |
| Rifapentine | N/A | Reduced | High | Inhibited | Reduced | Yes | N/A | Light Blue | Blue |
| Rifaximin | N/A | N/A | Reduced | Inhibited | Inhibited | Reduced | N/A | N/A | Clear |
| 5-Nonyloxyltryptamine | High | High | No Test | Reduced | Yes | No Test | Blue | Blue | No Test |
| Unidentified | High | High | No Test | Reduced | Yes | No Test | Blue | Blue | No Test |

Example 2—RFX is Effective Against Clinical Isolates of Gram-Negative and -Positive Bacteria and has a Synergy Activity with TOB or Amikacin Because RFX was not a traditional treatment for *P. aeruginosa* infections, it was first tested whether RFX was effective in vitro against *P. aeruginosa* and other bacterial pathogens seen in CF. Since RFX is not used for treatment of ventilator-associated pneumonia (VAP), it was thought the isolates of tracheal aspirates from VAP patients in the ICU may be sensitive to RFX. To determine the susceptibility to RFX, resistant isolates from the Cabell Huntington Hospital were chosen to measure the minimum inhibitory concentrations (MIC) for RFX (Table 3).

TABLE 3

Clinical isolates used for MIC testing.

| Clinical Bacterial Isolates | Genotype, phenotype, or resistance profile | Source |
|---|---|---|
| *P. aeruginosa* Isolates | | |
| K3050830 | Sputum Sample: Cipro, Gent, Levo, Mero, Tobra | CHH[a] |
| K3061403 | Sputum Sample: Aztre, Cefta, Cipro, Tobra, Gent, Levo, Mero, Pip | CHH[a] |
| K4040932 | Sputum Sample: Amik, Aztre, Gent, Levo | CHH[a] |
| K4130630 | Sputum Sample: Aztre, Cefta, Cefo, Pip | CHH[a] |
| K4111803 | Sputum Sample: Aztre, Cefta, Cipro, Tobra, Gent, Levo, Mero, Pip | CHH[a] |
| K5070734 | Sputum Sample: Aztre, Cefta, Cipro, Cefe, Tobra, Gent, Levo, Mero, Pip | CHH[a] |
| K6150790a | Sputum Sample: Aztre, Cefta, Cipro, Cefe, Tobra, Gent, Levo, Mero, Pip | CHH[a] |
| K6150790b | Sputum Sample: Aztre, Cefta, Cefe, Pip | CHH[a] |
| K5180948 | Sputum Sample: Aztre, Cefta, Cipro, Cefe, Tobra, Gent, Levo, Mero, Pip | CHH[a] |
| K5211493 | Sputum Sample: Aztre, Cipro, Levo, Mero | CHH[a] |
| K5230948 | Sputum Sample: Aztre, Cipro, Levo, Mero | CHH[a] |
| K5311090 | Sputum Sample: Aztre, Cefta, Cipro, Cefe, Tobra, Gent, Levo, Mero, Pip | CHH[a] |
| K6150501 | Sputum Sample: Cipro, Levo | CHH[a] |
| K7021701a | Sputum Sample: Aztre, Cipro, Tobra, Gent, Levo, Mero | CHH[a] |
| K7021701b | Sputum Sample: Aztre, Cefta, Cipro, Tobra, Gent, Levo, Mero, Pip | CHH[a] |
| K7041915b | Sputum Sample: Aztre, Cefta, Cipro, Cefe, Tobra, Gent, Levo, Mero, Pip | CHH[a] |
| K8040645b | Sputum Sample: Aztre, Levo, Mero | CHH[a] |
| K8061883b | Sputum Sample: Cipro, Levo | CHH[a] |
| K8061883c | Sputum Sample: Amik, Gent | CHH[a] |
| K8081410a | Sputum Sample: Aztre, Cefta | CHH[a] |
| 0232 | aadA6, OXA-50, PAO, strA, strB, sul1, tet(C) | CDC[b] |
| 0241 | aac (6')-IIc, aadA7, catB7, IMP-1, OXA-101, OXA-50, OXA-9, PAO, sul1 | CDC[b] |
| 0242 | aac (3)-Id, aadA2, cm1A1, dfrB5, OXA-4, OXA-50, PAO, VIM-2 | CDC[b] |
| 0246 | aadB, NDM-1, OXA-10, OXA-50, PAO, rmtD2, tet(G)tim, VEB-1 | CDC[b] |
| 0248 | aac (3)-Id, aadA2, cm1A1, dfrB5, OXA-4, OXA-50, PAO, tet(G), VIM-2 | CDC[b] |
| 0265 | aadB, catB7, OXA-50, PAO | CDC[b] |
| *S. aureus* Isolates | | |
| K3030365 | Sputum Sample: Amp, Amox, Clinda, Cipro, Eryth, Levo, Meth, Oxa, Pen, Trim | CHH[a] |
| K3051765 | Sputum Sample: Amp, Amox, Clinda, Cipro, Eryth, Levo, Oxa, Pen | CHH[a] |

TABLE 3-continued

Clinical isolates used for MIC testing.

| Clinical Bacterial Isolates | Genotype, phenotype, or resistance profile | Source |
|---|---|---|
| K3171696 | Sputum Sample: Amp, Amox, Cipro, Eryth, Levo, Meth, Oxa, Pen | CHH[a] |
| K3171648 | Sputum Sample: Amp, Amo, Clinda, Cipro, Eryth, Levo, Meth, Oxa, Pen | CHH[a] |
| K3211227 | Sputum Sample: Amp, Amox, Cipro, Eryth, Levo, Meth, Oxa, Pen | CHH[a] |
| K3251277 | Sputum Sample: Amp, Amox, Cipro, Eryth, Levo, Meth, Oxa, Pen | CHH[a] |
| K3270906 | Sputum Sample: Amp, Amox, Cipro, Eryth, Meth, Oxa, Pen | CHH[a] |
| K3300507 | Sputum Sample: Amp, Amox, Cipro, Eryth, Meth, Oxa, Pen | CHH[a] |
| K4010571 | Sputum Sample: Amp, Amox, Eryth, Meth, Oxa, Pen | CHH[a] |
| K5090899 | Brochial Wash: Amp, Amox, Clinda, Cipro, Eryth, Levo, Meth, Oxa, Pen | CHH[a] |
| K5091554 | Sputum Sample: Amp, Amox, Clinda, Cipro, Eryth, Levo, Meth, Oxa, Pen | CHH[a] |
| K5121709 | Tracheal Aspirate: Amp, Amox, Clinda, Cipro, Eryth, Levo, Meth, Oxa, Pen | CHH[a] |
| K5150830 | Sputum Sample: Amp, Clinda, Eryth, Pen | CHH[a] |
| K5160682 | Sputum Sample: Amp, Pen | CHH[a] |
| K5160792 | Sputum Sample: Amp, Amo, Clin, Eryth, Meth, Oxa, Pen | CHH[a] |
| K5180796 | Sputum Sample: Amp, Amox, Clinda, Cipro, Eryth, Levo, Meth, Oxa, Pen, Trim, Tet | CHH[a] |
| K5221462 | Sputum Sample: Clinda, Eryth, Gent, Tet | CHH[a] |
| K5240801 | Sputum Sample: Susceptible | CHH[a] |
| K5281689 | Sputum Sample: Amp, Amox, Clinda, Cipro, Eryth, Meth, Oxa | CHH[a] |
| K5282054 | Sputum Sample: Amp, Amo, Eryth, Meth, Oxa, Pen | CHH[a] |
| JE2 parent | mecA, SCCmec IVa, USA 300, pvl+ | NARSA[c] |
| COL | mecA, SCCmec I | NARSA[c] |
| *A. baumannii* Isolates | | |
| K5311090 | Sputum Sample: Aztre, Cefta, Cipro, Cefe, Tobra, Gent, Levo, Mero, Pip | CHH[a] |
| K6150501 | Sputum Sample: Cipro, Levo | CHH[a] |
| K7021701a | Sputum Sample: Aztre, Cipro, Tobra, Gent, Levo, Mero | CHH[a] |
| K7021701b | Sputum Sample: Aztre, Cefta, Cipro, Tobra, Gent, Levo, Mero, Pip | CHH[a] |
| K7041915b | Sputum Sample: Aztre, Cefta, Cipro, Cefe, Tobra, Gent, Levo, Mero, Pip | CHH[a] |
| K8040645b | Sputum Sample: Aztre, Levo, Mero | CHH[a] |
| K8061883b | Sputum Sample: Cipro, Levo | CHH[a] |
| K8061883c | Sputum Sample: Amik, Gent | CHH[a] |
| K8081410a | Sputum Sample: Aztre, Cefta | CHH[a] |
| *B. cepacia* Isolates | | |
| BC702 | LMG 18941, ATCC BAA-246 | NIH[d] |
| BC707 | UCB 717, ATCC 25416 | NIH[d] |

[a]Cabell Huntington Hospital Patient Samples, Huntington, WV,
[b]CDC Antimicrobial Resistance Isolate Bank,
[c]Network on Antimicrobial Resistance in *Staphylococcus aureus* (NARSA),
[d]NIH Biodefense and Emerging Infections Research Resources Repository
*All none ATCC strains used for MIC work listed above.
Amik = Amikacin;
Amox = Amoxicillin;
Amp = Ampicillin;
Aztreo = Aztreonam;
Cefta = Ceftazidime;
Cefe = Cefepime;
Cipro = Ciprofloxacin;
Clinda = Clindamycin;
Eryth = Erythromycin;
Gent = Gentamicin;
Levo = Levofloxacin;
Mero = Meropenem;
Meth = Methicillin;
Oxa = Oxacillin;
Pen = Penicillin;
Pip = Piperacillin;
Tob = TOB;
Trim = Trimethoprim
(Indicates Strain Resistance to specified Antimicrobials)

The $MIC_{50}$ and $MIC_{90}$ for multidrug resistant (MDR) *Staphylococcus aureus* including methicillin-resistant *S. aureus* (MRSA) was determined to be 2 and 16 μg/mL, respectively (Table 4). The $MIC_{50}$ and $MIC_{90}$ for MDR *P. aeruginosa* was determined to be 8 and 16 μg/mL, respectively (Table 4). The MICs of RFX were also determined for other drug-resistant pathogens that were associated with CF and VAP. It was found that RFX can effectively inhibit the growth of clinical isolates of *Burkholderia cepacia, Acinteboacter baumannii* and *Stenotrophomonas maltophilia* (Table 4).

TABLE 4

Determination of RFX MICs against clinical isolates of MDR bacterial species.

| Bacterial species | # Strains tested | $MIC_{50}$ (mg/L) | $MIC_{90}$ (mg/L) |
|---|---|---|---|
| *Pseudomonas aeruginosa* | 26 | 8 | 16 |
| *Staphylococcus aureus* | 22 | 2 | 16 |
| *Acinetobacter baumannii* | 9 | <0.5 | <0.5 |

TABLE 4-continued

Determination of RFX MICs against clinical isolates of MDR bacterial species.

| Bacterial species | # Strains tested | MIC$_{50}$ (mg/L) | MIC$_{90}$ (mg/L) |
|---|---|---|---|
| Burkholderia cepacia | 4 | 16 | 32 |
| Stenotrophomonas maltophilia | 1 | 16 | 16 |

Sources of clinical isolates is listed in Table 4. MIC$_{50}$ and MIC$_{90}$ are the concentrations of RFX required for the growth inhibition of 50% and 90% of strains, respectively.

RFX is a member of the rifamycins family of antibiotics. Its function is to inhibit the transcription by bacterial RNA polymerase; however, the mutations in the gene encoding the bacterial RNA polymerase frequently emerge. To increase the efficacy of this group of antibiotics, it was determined whether RFX can be used in combination with antipseudomonal antibiotics to reduce the frequency of resistant mutations. Checkerboard (isobologram) analysis with RFX and TOB combinations showed synergistic (ΣFIC≤0.5) or additive (ΣFIC 0.5< to ≤1) effects in all the strains tested (Table 5). In the final analysis, RFX was found to be a candidate for further study as an antibiotic adjuvant for the treatment of respiratory infections due to MDR pathogens.

TABLE 5

Minimum inhibitory concentrations and synergy activity of RFX and TOB against *P. aeruginosa* strains.

| Strain | Type | MIC RFX | MIC RFX in Combination | FIC RFX | MIC TOB | MIC TOB in Combination | FIC TOB | ΣFIC | Activity |
|---|---|---|---|---|---|---|---|---|---|
| PAO1 | NM | 16 | 4 | 0.25 | 2 | 0.25 | 0.125 | 0.375 | ++ |
| PAO581 | M | 16 | 4 | 0.25 | 2 | 0.5 | 0.25 | 0.5 | + |
| PAO581 | NM revertant | 16 | 4 | 0.25 | 2 | 0.5 | 0.25 | 0.5 | + |
| CF001 | M | 16 | 4 | 0.25 | 2 | 0.5 | 0.25 | 0.5 | + |
| CF010 | M | 8 | 2 | 0.25 | 2 | 0.5 | 0.25 | 0.5 | + |
| CF003 | NM | 4 | 1 | 0.25 | 2 | 0.25 | 0.125 | 0.375 | +c |

NM = Non-mucoid;
M = Mucoid
‡lowest ΣFIC measure: synergy (++) ≤0.5; additive (+) 0.5 < to ≤ 1; indifferent (±) 1 < to ≤ 4; antagonism (−) >4.

Example 3—RFX is More Effective than TOB in Inhibiting the Alginate Production in *P. aeruginosa*

Figure 1B:
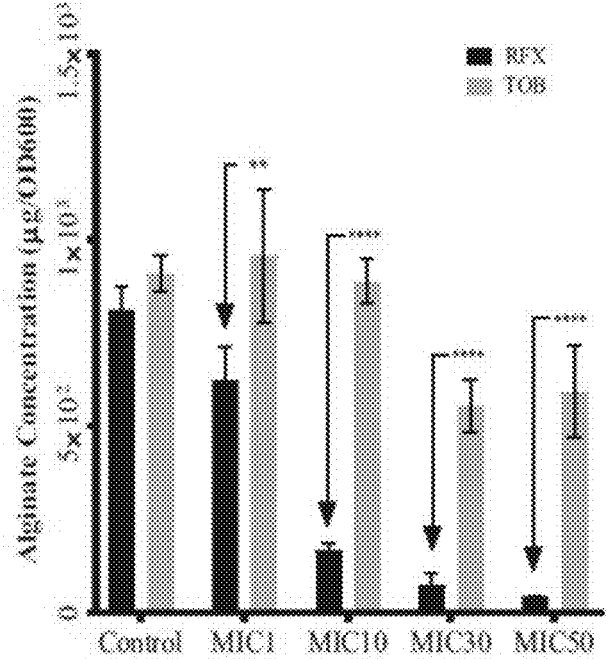
Figure 1C:
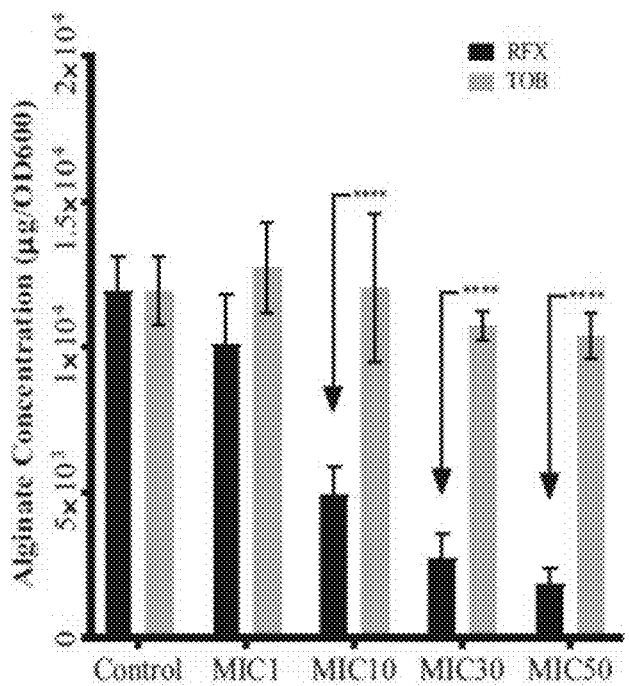
Figure 1D:
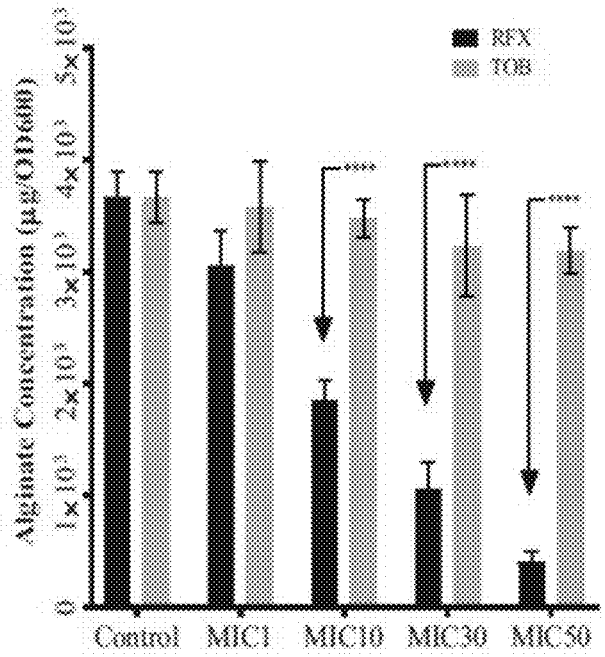

The results of the preliminary drug screening indicated that RFX may inhibit alginate biosynthesis. To investigate the extent of this inhibition, PAO1, PAO581, and two mucoid *P. aeruginosa* CF isolates (CF001 and CF010) were grew on PIA plates containing sub-MIC concentrations of either TOB or RFX and measured alginate production with the carbazole assay. These isolates were chosen because they had a similar MIC range for RFX and TOB and were still sensitive to TOB. The MIC normalization was used to compare the effect of the two drugs on inhibition of alginate production, as this allowed the measurement of alginate made by the same number of bacterial cells. Using this method, there was no significant difference in alginate production by the non-mucoid strain PAO1 when treated with TOB or RFX at any concentration (FIG. 1A). Conversely, RFX significantly decreased alginate production in the mucoid PAO581 strain at all concentrations tested, as compared to TOB in mucoid strain PAO581 (FIG. 1B). A significant decrease in alginate production was further observed in the mucoid CF isolates CF001 and CF010 as compared to TOB (FIGS. 1C-1D). These results indicated that RFX was more effective than TOB at inhibiting the alginate production in mucoid strains of *P. aeruginosa*.

Figure 2A:
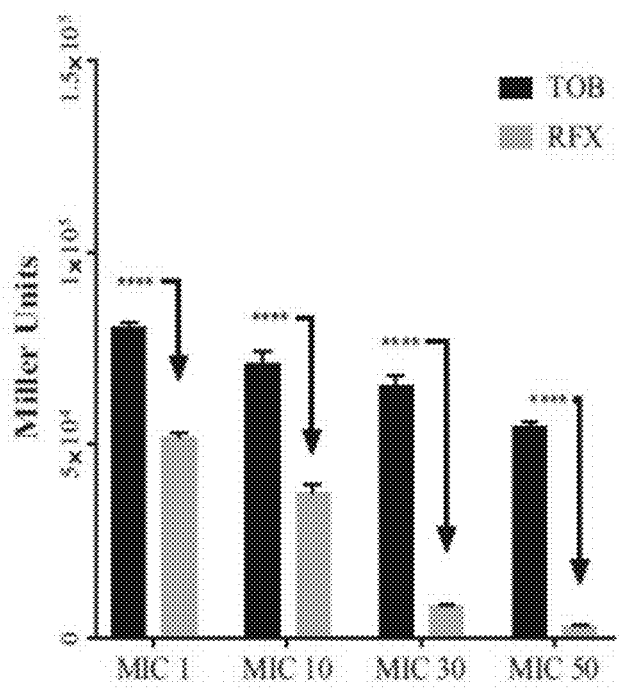
FIGS. 2A-2C include graphs showing RFX versus TOB mediated inhibition of the promoter $P_{algD}$ activity of the alginate biosynthetic operon in laboratory and clinical isolates of *P. aeruginosa*. The β-galactosidase activity of $P_{algD}$ was measured using the pLP170-$P_{algD}$-lacZ reporter construct in PAO581 (FIG. 2A), CF001 (FIG. 2B), and CF010 (FIG. 2C) grown on PIA plates with increasing concentrations of RFX or TOB (MIC1, MIC10, MIC30, MIC50) at 37° C. for 24 h. Relative expression mean values are shown ±SE of triplicate determinations. Two-way ANOVA was used to determine statistical significance set at a P value of <0.01 (****, P<0.0001).
Figure 2B:
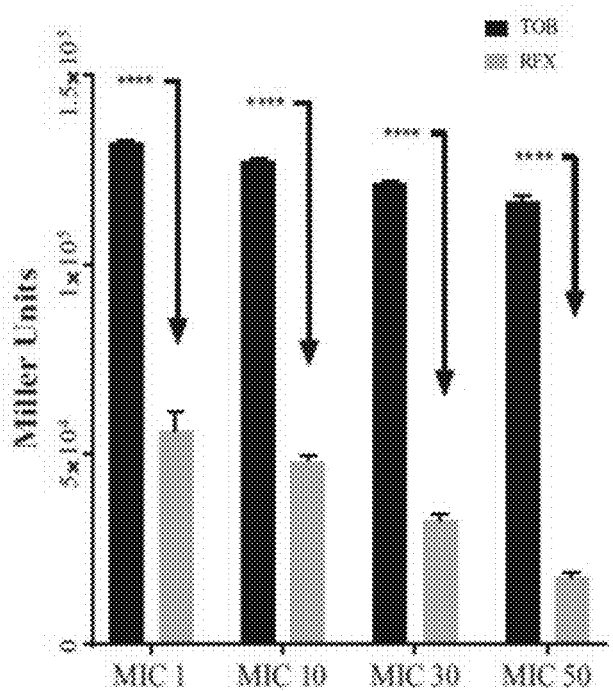
Figure 2C:
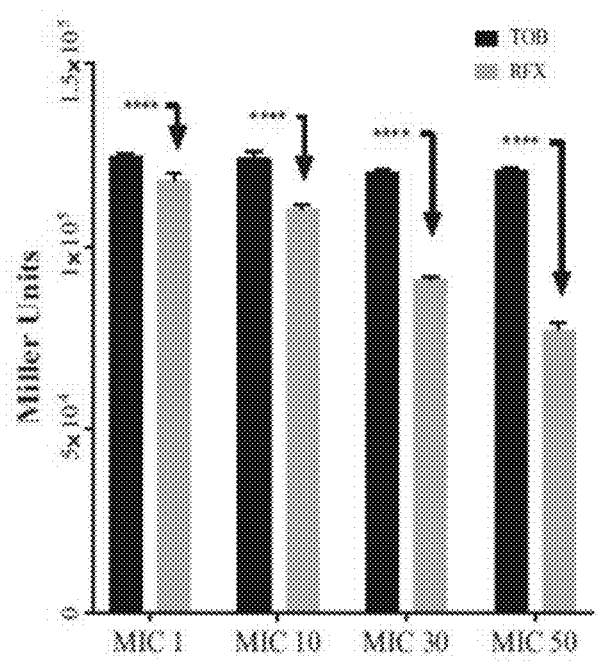

While RFX inhibits alginate production, additional experiments were conducted to determine whether the inhibition was specific to alginate or whether it was a global suppression of transcription. To test this, the promoter reporter constructs P$_{algD}$ lacZ in pLP170 were used to quantify the promoter activity of the alginate biosynthetic operon P$_{algD}$. A promoter-less empty vector pLP170-lacZ was used as a negative control. Using the β-galactosidase reporter activity, the activity of P$_{algD}$ in PAO581 was quantified (FIG. 2A), and two mucoid isolates (CF001 and CF010) from CF patients. When grown in PIA containing various concentrations of RFX or TOB (FIGS. 2B-2C), RFX had a more pronounced effect on promoter activity than TOB throughout the entire concentration range in all three tested strains. Based on these data, it was believed that RFX inhibits alginate biosynthesis by antagonizing transcription.

Figure 3A:
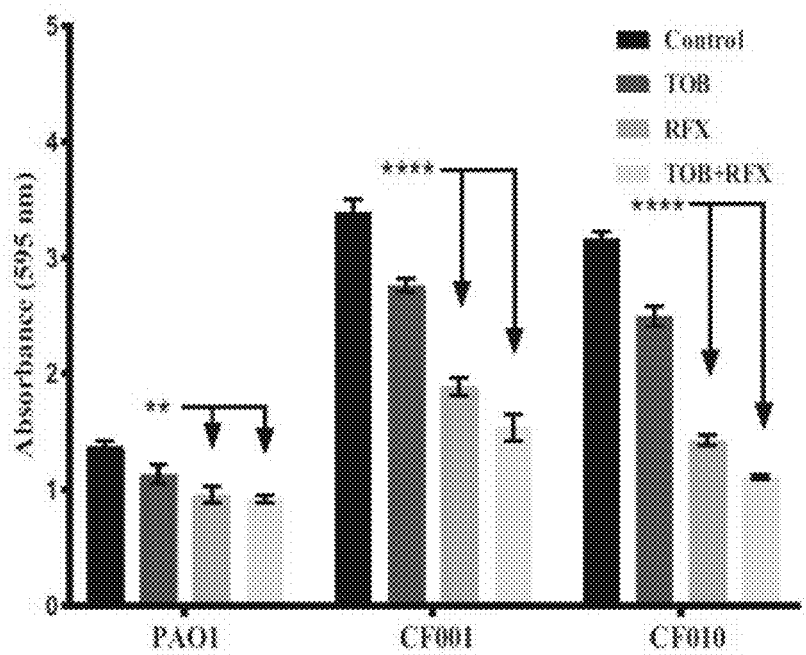
FIGS. 3A-3B include graphs showing biofilm and cell viability reduction from treatment with TOB and/or RFX, where (FIG. 3A) biofilms were grown for 24 h in a 96-well plate and then treated with TOB, RFX, or TOB and RFX at a concentration of 3×MIC, or where (FIG. 3B) biofilms were grown for 24 h in a 96-well plate and then treated with TOB, RFX, or TOB and RFX at concentration of 3×MIC. Two-way ANOVA analysis was used with statistical significance set as a P value of <0.01 (**, P<0.0001; , P<0.001; *, P<0.01).
Figure 3B:
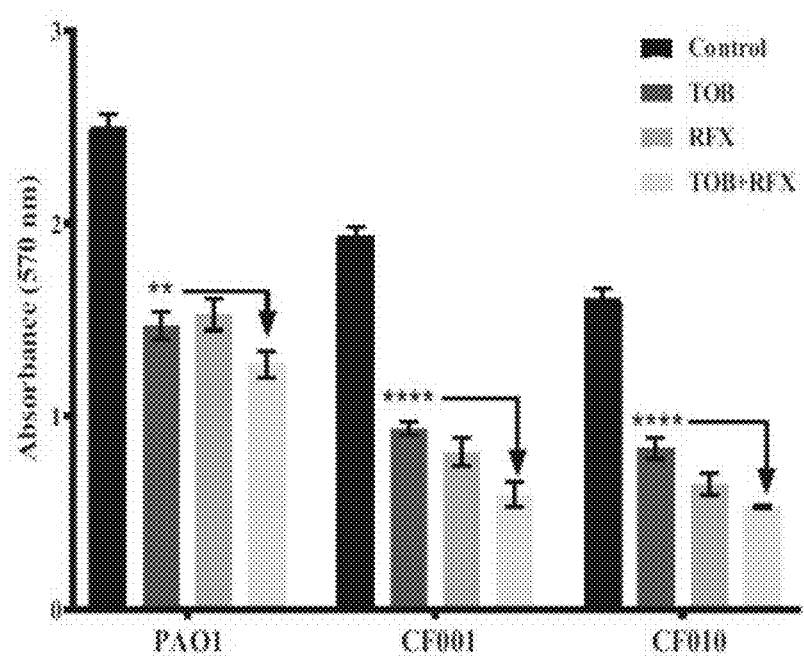
Figure 4:
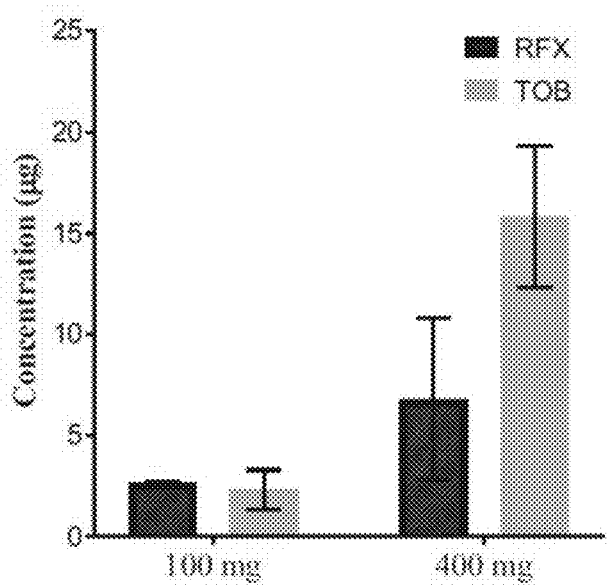
FIG. 4 is a graph showing a comparison of the levels of RFX and TOB delivered via nebulization in mouse lungs. The concentration of RFX or TOB present in lungs of C57BL/6 mice immediately after treatment with 100 or 400 mg of the respective antibiotics. Data shown represent means of 4 lung samples with replicates totaling 8 samples per group ±SE. One-way ANOVA was used to analyze the data with statistical significance set at a P value of <0.01. No significant differences were found between the RFX versus TOB concentrations present in the mouse lungs.
Figure 5A:
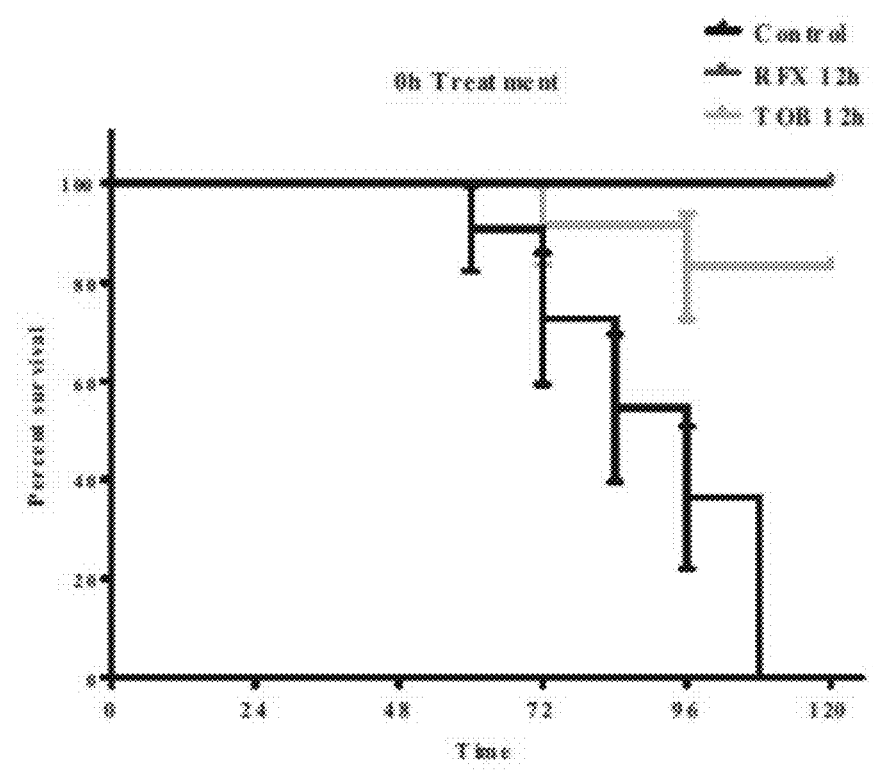
FIGS. 5A-5C include graphs showing RFX is more effective than TOB in the treatment of *P. aeruginosa* infection in mice. Kaplan-Meier curves showing percent survival of DBA/2 mice with *P. aeruginosa* PAO1 infection after treatment with RFX or TOB at 0 h post-infection (FIG. 5A), 6 h post-infection (FIG. 5B), and 12 h post-infection (FIG. 5C). Data shown represent means of 12 mice per group. The Mantel-Cox test was used with significance set at a P value of <0.01 and showing standard error (SE) bars.
Figure 5B:
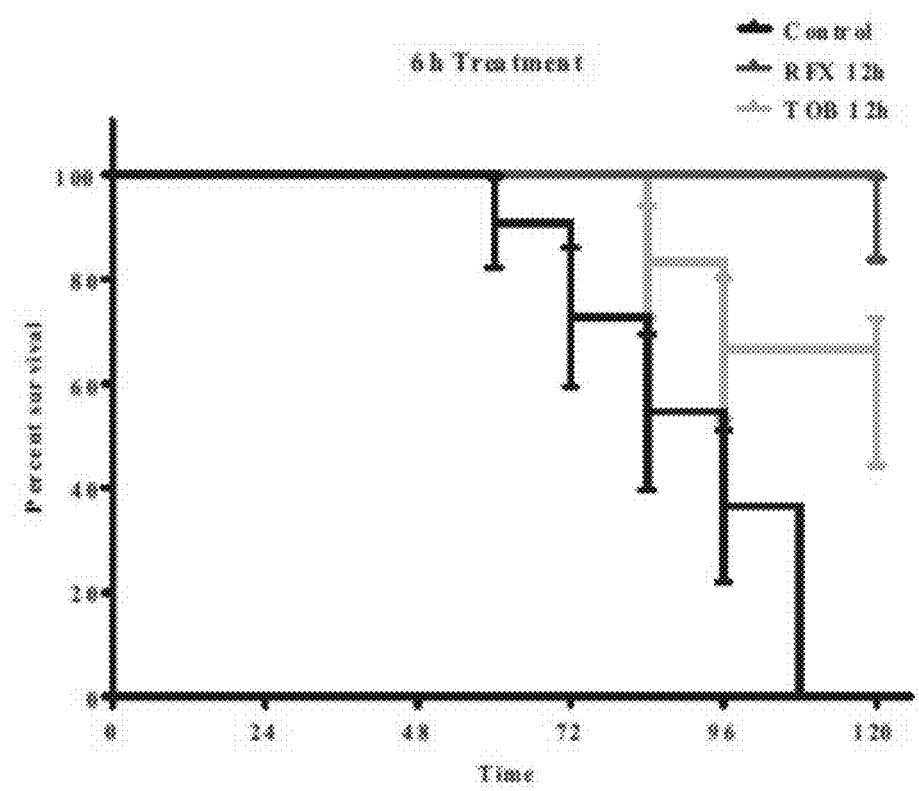
Figure 5C:
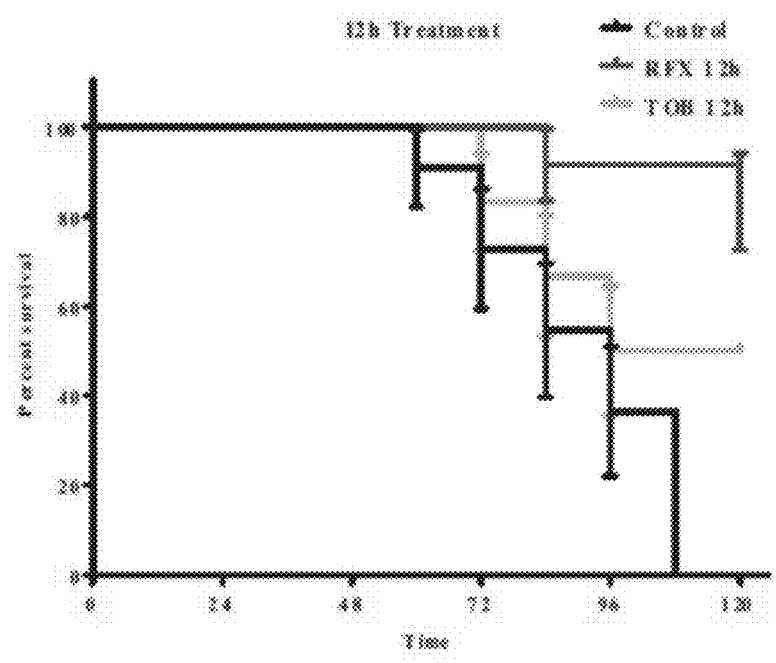
Figure 6:
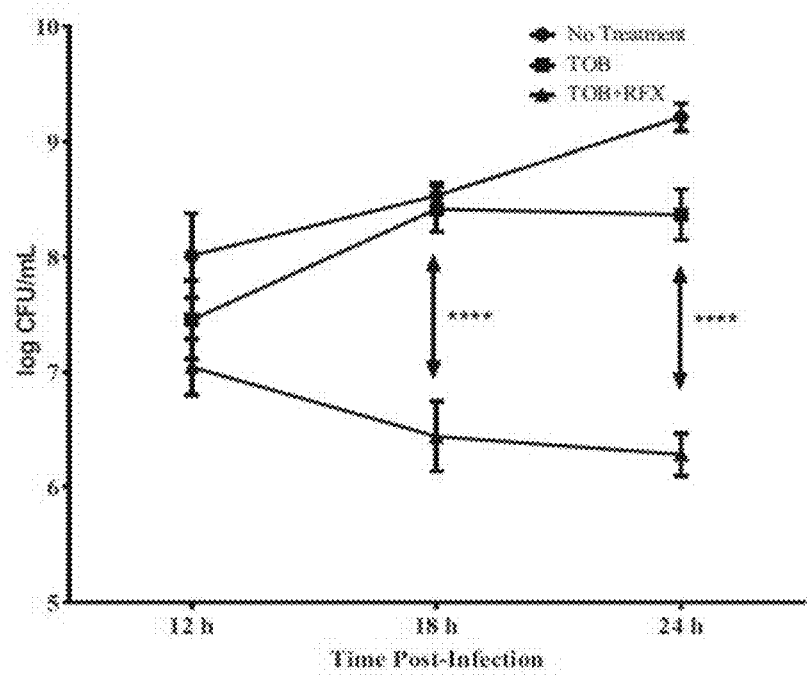
FIG. 6 is a graph showing that the addition of RFX to multiple treatments of TOB results in a decrease of CFU per milliliter of *P. aeruginosa* in mouse lungs. Plot showing the CFU per milliliter counts of mice after being infected with *P. aeruginosa* and left untreated, treated with multiple doses of TOB, or treated with multiple doses of TOB with addition of RFX. Data shown represent average of 2 mice per time point per group. Two-way ANOVA was used to test for statistical significance with a P value of <0.01 (****, P<0.0001).

Example 4—TOB with the Addition of RFX Reduces the Biofilm Aggregates and Viable Cell Counts Since RFX inhibited alginate production, the ability of RFX to reduce biofilm aggregates, defined as a decrease in preformed biofilm, was then tested along with the biofilm viable cell counts. An established biofilm reduction assay was performed with viable cell counts using PAO1 and mucoid clinical isolates CF001 and CF010. TOB significantly reduced biofilm as compared to the untreated control (FIG. 3A). However, TOB with the addition of RFX significantly reduced the biofilm aggregates as compared to TOB alone. Furthermore, TOB significantly reduced the number of viable cells in a preformed biofilm as compared to the untreated control. The addition of RFX with TOB significantly reduced this number further, enhancing the efficacy of TOB alone (FIG. 3B). This provides evidence that the addition of RFX helps TOB penetrate biofilms and decrease biofilm viable cell counts.

Example 5—RFX can be Delivered to the Lungs Via Nebulization

As treatment for traveler's diarrhea, RFX is a drug optimized for oral use. For RFX to be useful as a treatment for CF patients, it was determined whether RFX could be delivered to the lungs through nebulization. Nebulizing RFX was initially unsuccessful and more difficult than presumed. Initially attempts were made to dissolve RFX in PBS or saline, but RFX did not dissolve in those solvents. RFX was not soluble in water-based solutions, but was soluble in dimethyl-sulfoxide (DMSO) and ETOH (ethanol) in small volumes. It was possible to partially or fully dissolve RFX in 20%, 40%, and 80% DMSO in PBS, but once attempts were made to nebulize those mixtures, the RFX would come out of solution and it was not possible to detect or determine any delivery of RFX to the lungs using those mixtures. However, 100% DMSO could be used to retain RFX in solution and deliver to the lungs as noted by HPLC data.

In short, the physiochemical properties made RFX only sparingly soluble in water, and therefore, DMSO was evaluated as a nebulization vehicle. The potential adverse effects of using DMSO were first assessed by nebulizing DMSO alone to a group of C57BL/6 mice (n=8). This type of mice was used due to their natural resistance against infection based on our previous studies. Exposure to a single dose of 5 ml of 100% DMSO caused no adverse effects. One month after exposure, all exposed mice were alive with body weights comparable to the PBS-treated control mice. Next, the delivery of both RFX and TOB via nebulization was optimized. RFX or TOB was delivered to the lungs of C57BL/6 mice (n=16) using a pressure-based nebulizer and whole-body exposure chamber with targeted delivery concentrations of 100 mg or 400 mg per mouse lungs (weight estimated to be 200 mg per mouse lung). These two concentrations were chosen as the current approved clinical treatment for nebulization therapy in human CF is 300 mg TOB nebulized in 5 ml 0.225% saline. Thus, both RFX and TOB were naturally respired by the mice. To determine the dosage of each drug received by the mice, the lungs were homogenized and drug concentrations of TOB and RFX were determined via ELISA and HPLC, respectively. RFX and TOB were present in the lungs at similar concentrations after the 100 mg nebulization (FIG. 4); however, at 400 mg nebulization, TOB exhibited non-statistically significant increase in lung concentration over RFX. These results indicated that nebulization can deliver both drugs to the mouse lung at a low dose (100 mg), but TOB may penetrate the lung tissues more efficiently than RFX at a high dose (400 mg). To determine variance of drug delivery caused by difference in solvents, particle size analysis was done using both drugs. The droplet size for both TOB and RFX were determined to be identical with the average droplet size for TOB and RFX being 5.07 μm and 5.02 μm, respectively.

Example 6—RFX Effectively Treats *P. aeruginosa* Infection in Mice

After establishing the dosing of TOB or RFX to efficiently reach the lungs, the efficacy of both drugs against *P. aeruginosa* lung infections was compared using an established mouse model. DBA/2 (n=84) male mice were first infected with aerosolized *P. aeruginosa* PAO1 in a whole-body exposure chamber as previously described. The mice were then separated into four groups. One group was left untreated to determine the rate of mortality (control). The remaining three groups were treated with RFX or TOB using a pressure-based nebulizer and whole-body exposure chamber at a concentration of 300 mg at 0 h, 6 h, or 12 h post infection. All control mice died within 5 days (FIGS. 5A-5C), consistent with what was previously reported. Treatment with RFX or TOB at 0 h after infection resulted in 100% and 92% survival, respectively (FIG. 5A). At 6 h post infection, treatment of RFX resulted in 92% survival, while 58% of mice treated with TOB survived (FIG. 5B). In the 12 h treatment group, 83% of mice treated with RFX survived, while only 50% of mice treated with TOB survived (FIG. 5C). Thus, RFX treatment after *P. aeruginosa* lung infection resulted in a higher survival and recovery rate than TOB treatment in a mouse lung infection model.

Example 7—The Addition of RFX to Multiple Treatments of TOB Reduces *P. Aeruginosa* Growth in Lungs of Mice Based on the efficacy seen with the single dose treatment a multiple dose study was used to replicate clinical treatment conditions seen with CF infections. The efficacy of TOB in multiple doses with or without RFX was determined using the established lung infection model. DBA/2 (n=24) female mice were exposed to aerosolized *P. aeruginosa* PAO1 with a chromosomal bioluminescent operon (luxCDABE) as described previously. A bioluminescent PAO1 was used to track the respiratory bacterial load as well as determine the presence of the lung normal flora. The mice were then separated into three groups of 8: one group was untreated, one group received three TOB treatments, and one group received an initial RFX treatment followed by two TOB treatments. The group without treatment had the highest amount of bacterial load with growth increasing to a maximum of $10^9$ CFUs at 24 h post infection (FIG. 6). Multiple treatments of TOB reduced the amount of bacterial growth in the lungs and kept the growth steady at around $10^8$ CFUs. With the addition of RFX to the doses of TOB, growth was further reduced and kept consistent at $10^6$ CFUs. All colonies isolated from the lung homogenates of the infected mice were bioluminescent suggesting that the total bacterial load resulted from the initial infection.

Discussion of Examples 1-7

Biofilm formation by *P. aeruginosa* is a major risk factor for people suffering CF. Current treatment includes the repeated use of inhaled TOB. This antibiotic may not continue to be an effective treatment strategy due to emerging aminoglycoside resistance in *P. aeruginosa* due to the biofilm formation that results in decreased permeability of TOB. In this study, it was found that RFX, which has been approved for use in treatment of treat traveler's diarrhea, irritable bowel syndrome, and hepatic encephalopathy, has antibacterial activity against *P. aeruginosa* and other MDR bacterial pathogens and can inhibit alginate production. Furthermore, RFX was effective against other bacterial pathogens associated with respiratory infections in CF and patients with VAP. These data indicate that RFX may be an effective antibiotic adjuvant for respiratory infections in CF patients.

Previous research has shown that the efficacy of TOB is hindered by its inability to penetrate and inhibit biofilm production. Although a biofilm is a general description of the matrices produced by *P. aeruginosa* and has many components, alginate production was used as a representation of biofilm production in this study. Carbazole assays were performed using media containing either RFX or TOB to measure the inhibitory effect on alginate production. In all mucoid strains tested, RFX significantly decreased alginate production compared to TOB. This decrease in alginate production indicated that RFX can inhibit alginate biofilm production and enhance bacterial uptake of TOB by *P. aeruginosa* in CF patients.

Once determining the inhibition of alginate and decrease in biofilm production by TOB and/or RFX, the reduction of preformed biofilms and viable cell counts with *P. aeruginosa* strains PAO1, CF001, and CF010 was investigated to determine their efficacy. TOB alone significantly reduced biofilm aggregates and viable cell counts compared to untreated samples. However, TOB was more effective in combination with RFX, as both reduced biofilm aggregates and viable cell counts compared to TOB alone. This indicated that the addition of RFX may be a positive component to treating biofilm producing strains of *P. aeruginosa* by enhancing TOB biofilm penetration. Thus, patients with complications from biofilm producing species may benefit of the addition of RFX.

The unique physiochemical and pharmacokinetic (PK) properties compared to other rifamycins further led to a focus on RFX for in vivo study. Oral RFX has low solubility in water and achieves high intestinal concentrations due to poor absorption. It was, however, found that RFX was readily soluble in DMSO, which is a solvent that is used at low concentrations in chronic obstructive pulmonary patients (COPD) to alleviate tar build up due to smoking. However, recent studies suggest DMSO to be toxic and produce cellular apoptosis at low concentrations. To examine possible toxicity associated with DMSO inhalation, mice were exposed to 100% DMSO prior to testing the drugs, and no physical adverse effects (irritation, activity level, body weight, or death) were observed. Delivery of nebulized RFX in DMSO and TOB in saline was next compared in mice via inhalation in a whole-body exposure chamber. The nebulization exhibited low efficiency in which the concentrations of bacteria and drugs nebulized were significantly higher than the amount delivered into the lungs, but this was expected as the system relies on delivery of drugs via natural respiration. This method was used over intra-tracheal delivery due to the possibility of injury with the insertion of tracheal tubes that could be misinterpreted as adverse effects of RFX as well as the change in respiratory patterns while anesthetized. Importantly, the inhalational delivery of drugs was optimized by measuring the tissue level of drugs via HPLC and ELISA. At lower dosages, the drugs were delivered into the lung at a similar concentration; however, as the amount of the drug nebulized increased, TOB was found to be more concentrated than RFX in mouse lungs. This could be due to the low solubility and absorption of RFX in the lung. Droplet size analysis for both drugs revealed the drugs to be identical ruling out any variance caused by differences in particle size. Furthermore, the results indicated the drugs were able to deposit through the airway and lung with nebulizer operation to impact the therapeutic zone. Moreover, no adverse effects were observed in the RFX treated mice. The mice behaved normally and survived for several months after the nebulization until euthanasia. The data therefore indicated that RFX can be delivered to the lungs via nebulization at measurable levels.

After determining that RFX was deliverable via inhalation, therapeutic efficacy was tested using a *P. aeruginosa* pneumonia model. We used an acute lung infection mouse model that was caused through natural respiration of *P. aeruginosa* aerosol in mice. It was previously found that DBA/2 mouse is highly susceptible to the lung colonization by *P. aeruginosa* in comparison to other inbred mouse strains. Lung infections in DBA/2 mice with non-mucoid strains of *P. aeruginosa* PAO1 resulted in excessive infiltration of neutrophils to the mouse lungs followed by massive formation of edema. The mice typically die within 120 h after lung infection. In this study, this model was used to test the drug efficacy for treating *P. aeruginosa* respiratory infections in mouse. Overall, more mice survived after treatment with RFX than all other experimental groups. While the survival rate following the six-hour administration of TOB was less than the twelve-hour administration, this difference was attributable to only one less mouse surviving between test groups.

Once a single dose study determined the efficacy of TOB vs RFX, a multiple dose study was used to determine the effect of adding RFX to multiple treatments of TOB, which would correlate more with clinical treatment methods. The animal model for the multiple dose experiment was identical, with the exception that the *P. aeruginosa* strain PAO1 used had a stably expressed bioluminescent marker to help track the bacteria and to determine presence in a native microbiome. In this study, it was observed that the addition of RFX reduced bacterial growth compared to TOB alone. Bioluminescence was also conserved and seen in all colonies grown from lung homogenates indicating that no native bacteria were culturable. These results strengthened the idea that the addition of RFX would aid TOB in penetration of *P. aeruginosa* biofilm infections.

In summary, it was shown that RFX was a potential candidate to be used against known lung pathogens as a supplementary additive to the currently established TOB treatment. RFX was shown to efficiently reach the lungs and increase survival rates in *P. aeruginosa* lung infections in mice.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Aloush V, Navon-Venezia S, Seigman-Igra Y, Cabili S, Carmeli Y. 2006. Multidrug-resistant *Pseudomonas aeruginosa*: risk factors and clinical impact. Antimicrob Agents Chemother 50:43-8.
2. Boucher J C, Yu H, Mudd M H, Deretic V. 1997. Mucoid *Pseudomonas aeruginosa* in cystic fibrosis: characterization of muc mutations in clinical isolates and analysis of clearance in a mouse model of respiratory infection. Infect Immun 65:3838-46.
3. Nasirmoghadas P, Yadegari S, Moghim S, Esfahani B N, Fazeli H, Poursina F, Hosseininassab S A, Safaei H G. 2018. Evaluation of Biofilm Formation and Frequency of Multidrug-resistant and Extended Drug-resistant Strain in *Pseudomonas aeruginosa* Isolated from Burn Patients in Isfahan. Adv Biomed Res 7:61.
4. Head N E, Yu H. 2004. Cross-sectional analysis of clinical and environmental isolates of *Pseudomonas aeruginosa*: biofilm formation, virulence, and genome diversity. Infect Immun 72:133-44.
5. Ciofu O, Tolker-Nielsen T, Jensen P O, Wang H, Hoiby N. 2015. Antimicrobial resistance, respiratory tract infections and role of biofilms in lung infections in cystic fibrosis patients. Adv Drug Deliv Rev 85:7-23.
6. Yu H, Hanes M, Chrisp C E, Boucher J C, Deretic V. 1998. Microbial pathogenesis in cystic fibrosis: pulmonary clearance of mucoid *Pseudomonas aeruginosa* and inflammation in a mouse model of repeated respiratory challenge. Infect Immun 66:280-8.
7. Anderson G G, Moreau-Marquis S, Stanton B A, O'Toole G A. 2008. In vitro analysis of tobramycin-treated

*Pseudomonas aeruginosa* biofilms on cystic fibrosis-derived airway epithelial cells. Infect Immun 76:1423-33.
8. Nichols W W, Dorrington S M, Slack M P, Walmsley H L. 1988. Inhibition of tobramycin diffusion by binding to alginate. Antimicrob Agents Chemother 32:518-23.
9. Hoffman L R, D'Argenio D A, MacCoss M J, Zhang Z, Jones R A, Miller S I. 2005. Aminoglycoside antibiotics induce bacterial biofilm formation. Nature 436:1171-5.
10. MacLeod D L, Nelson L E, Shawar R M, Lin B B, Lockwood L G, Dirk J E, Miller G H, Burns J L, Garber R L. 2000. Aminoglycoside-resistance mechanisms for cystic fibrosis *Pseudomonas aeruginosa* isolates are unchanged by long-term, intermittent, inhaled tobramycin treatment. J Infect Dis 181:1180-4.
11. Iorio N, Malik Z, Schey R. 2015. Profile of rifaximin and its potential in the treatment of irritable bowel syndrome. Clin Exp Gastroenterol 8:159-67.
12. Mullen K, Prakash R. 2010. Rifaximin for the treatment of hepatic encephalopathy. Expert Rev Gastroenterol Hepatol 4:665-77.
13. Mullen K D, Sanyal A J, Bass N M, Poordad F F, Sheikh M Y, Frederick R T, Bortey E, Forbes W P. 2014. Rifaximin is safe and well tolerated for long-term maintenance of remission from overt hepatic encephalopathy. Clin Gastroenterol Hepatol 12:1390-7 e2.
14. Brown E L, Xue Q, Jiang Z D, Xu Y, Dupont H L. 2010. Pretreatment of epithelial cells with rifaximin alters bacterial attachment and internalization profiles. Antimicrob Agents Chemother 54:388-96.
15. Ricci A, Coppo E, Barbieri R, Debbia E A, Marchese A. 2017. The effect of sub-inhibitory concentrations of rifaximin on urease production and on other virulence factors expressed by *Klebsiella pneumoniae, Proteus mirabilis, Pseudomonas aeruginosa* and *Staphylococcus aureus*. J Chemother 29:67-73.
16. Rothstein J D, Patel S, Regan M R, Haenggeli C, Huang Y H, Bergles D E, Jin L, Dykes Hoberg M, Vidensky S, Chung D S, Toan S V, Bruijn L I, Su Z Z, Gupta P, Fisher P B. 2005. Beta-lactam antibiotics offer neuroprotection by increasing glutamate transporter expression. Nature 433:73-7.
17. Stavrovskaya I G, Narayanan M V, Zhang W, Krasnikov B F, Heemskerk J, Young S S, Blass J P, Brown A M, Beal M F, Friedlander R M, Kristal B S. 2004. Clinically approved heterocyclics act on a mitochondrial target and reduce stroke-induced pathology. J Exp Med 200:211-22.
18. Cao B, Christophersen L, Kolpen M, Jensen P O, Sneppen K, Hoiby N, Moser C, Sams T. 2016. Diffusion Retardation by Binding of Tobramycin in an Alginate Biofilm Model. PLoS One 11:e0153616.
19. Long T E, Keding L C, Lewis D D, Anstead M I, Withers T R, Yu H D. 2016. Anionic fluoroquinolones as antibacterials against biofilm-producing *Pseudomonas aeruginosa*. Bioorg Med Chem Lett 26:1305-9.
20. Ryan Withers T, Heath Damron F, Yin Y, Yu H D. 2013. Truncation of type IV pilin induces mucoidy in *Pseudomonas aeruginosa* strain PAO579. Microbiologyopen 2:459-70.
21. Isenberg H D, American Society for Microbiology. 2004. Clinical microbiology procedures handbook, 2nd ed. ASM Press, Washington, D.C.
22. Moody J. 1992. Synergy testing: broth microdilution checkerboard and broth macrodilution methods, p 5.18.1-5.18.23. In Eisenberg H (ed), Clinical microbiology procedures handbook. American Society for Microbiology, Washington D.C.
23. Al Ahmar R, Kirby B D, Yu H D. 2018. Pyrimidine Biosynthesis Regulates Small Colony Variant and Mucoidy in *Pseudomonas aeruginosa* Through Sigma Factor Competition. J Bacteriol doi:10.1128/JB.00575-18.
24. Sheppard J G, McAleer J P, Saralkar P, Geldenhuys W J, Long T E. 2018. Allicin-inspired pyridyl disulfides as antimicrobial agents for multidrug-resistant *Staphylococcus aureus*. Eur J Med Chem 143:1185-1195.
25. Wilson K R, Napper J M, Denvir J, Sollars V E, Yu H D. 2007. Defect in early lung defence against *Pseudomonas aeruginosa* in DBA/2 mice is associated with acute inflammatory lung injury and reduced bactericidal activity in naive macrophages. Microbiology 153:968-79.
26. Yu H, Head N E. 2002. Persistent infections and immunity in cystic fibrosis. Front Biosci 7:d442-57.
27. Hoiby N, Ciofu O, Bjarnsholt T. 2010. *Pseudomonas aeruginosa* biofilms in cystic fibrosis. Future Microbiol 5:1663-74.
28. Kimura R, Traber L D, Herndon D N, Neuhaus G D, Traber D L. 1988. Treatment of smoke-induced pulmonary injury with nebulized dimethylsulfoxide. Circ Shock 25:333-41.
29. Galvao J, Davis B, Tilley M, Normando E, Duchen M R, Cordeiro M F. 2014. Unexpected low-dose toxicity of the universal solvent DMSO. FASEB J 28:1317-30.
30. Knutson C A, Jeanes A. 1968. A new modification of the carbazole analysis: application to heteropolysaccharides. Anal Biochem 24:470-81.
31. Sachetelli S, Beaulac C, Lagace J. 1998. Aminoglycoside detection using a universal ELISA binding procedure onto polystyrene microtiter plates in comparison with HPLC analysis and microbiological agar-diffusion assay. Biochim Biophys Acta 1379:35-41.
32. Rao R N, Vali R M, Rao A V. 2012. Determination of rifaximin in rat serum by ionic liquid based dispersive liquid-liquid microextraction combined with RP-HPLC. J Sep Sci 35:1945-52.
33. Figurski D H, Helinski D R. 1979. Figurski, D. H. & Helinski, D. R. Replication of an origin-containing derivative of plasmid RK2 dependent on a plasmid function provided in trans. Proc. Natl. Acad. Sci. USA 76, 1648-1652, vol 76.
34. Figurski D H, Helinski D R. 1979. Replication of an origin-containing derivative of plasmid RK2 dependent on a plasmid function provided in trans. Proceedings of the National Academy of Sciences of the United States of America 76:1648-1652.
35. Preston M J, Seed P C, Toder D S, Iglewski B H, Ohman D E, Gustin J K, Goldberg J B, Pier G B. 1997. Contribution of proteases and LasR to the virulence of *Pseudomonas aeruginosa* during corneal infections. Infection and Immunity 65:3086-3090.
36. Choi K H, Schweizer H P. 2006. mini-Tn7 insertion in bacteria with single attTn7 sites: example *Pseudomonas aeruginosa*. Nat Protoc 1:153-61.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:
1. A method of treating a bacterial lung infection, comprising administering to a subject in need thereof an effective amount of rifaximin by inhalation delivery, wherein the rifaximin is in aerosolized form.

2. The method of claim 1, wherein the bacterial lung infection comprises an antibiotic-resistant bacterial lung infection.

3. The method of claim 1, wherein the bacterial lung infection comprises an infection by a bacteria selected from the group consisting of *Pseudomonas aeruginosa, Staphylococcus aureus, Burkholderia cepacia*, and *Stenotrophomonas maltophilia*.

4. The method of claim 1, further comprising co-administering an effective amount of tobramycin to the subject.

5. The method of claim 4, wherein the rifaximin and/or the tobramycin are administered in multiple doses.

6. The method of claim 4, wherein the tobramycin is in aerosolized form.

7. The method of claim 1, wherein the bacterial lung infection is acute pneumonia.

8. The method of claim 1, wherein the subject has a bacterial lung infection.

9. The method of claim 1, wherein the subject has cystic fibrosis.

10. The method of claim 1, wherein administering the rifaximin reduces an amount of biofilm produced from the bacterial lung infection.

11. The method of claim 1, wherein the rifaximin is administered in an amount effective to reduce an amount of alginate production.

12. A method of reducing biofilm formation, comprising contacting a bacteria with an effective amount of rifaximin and an effective amount of tobramycin by inhalation delivery, wherein the rifaximin and the tobramycin are in aerosolized form.

13. The method of claim 12, wherein the bacteria comprises an antibiotic-resistant bacteria.

14. The method of claim 12, wherein the bacteria is selected from the group consisting of *Pseudomonas aeruginosa, Staphylococcus aureus, Burkholderia cepacia*, and *Stenotrophomonas maltophilia*.

15. The method of claim 12, wherein the rifaximin and/or tobramycin are administered in multiple doses.

* * * * *